(12) United States Patent
Sawkey et al.

(10) Patent No.: US 10,776,534 B2
(45) Date of Patent: Sep. 15, 2020

(54) LINAC SIMULATOR

(71) Applicant: Varian Medical Systems, Inc., Palo Alto, CA (US)

(72) Inventors: Daren Sawkey, Palo Alto, CA (US); Ioan Antoniu Popescu, Vancouver (CA); Michelle M. Svatos, Oakland, CA (US); Corey Zankowski, San Jose, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 843 days.

(21) Appl. No.: 15/087,295

(22) Filed: Mar. 31, 2016

(65) Prior Publication Data

US 2017/0286573 A1 Oct. 5, 2017

(51) Int. Cl.
*G06F 30/20* (2020.01)
*G06F 30/12* (2020.01)
*G06F 17/18* (2006.01)

(52) U.S. Cl.
CPC .............. *G06F 30/20* (2020.01); *G06F 17/18* (2013.01); *G06F 30/12* (2020.01)

(58) Field of Classification Search
CPC ........ A61N 5/103; A61N 5/1071; G06F 30/12
USPC ........................... 703/22, 24; 706/11; 378/65
See application file for complete search history.

(56) References Cited

U.S. PATENT DOCUMENTS

| 7,016,522 | B2 | 3/2006 | Bani-Hashemi | |
|---|---|---|---|---|
| 7,487,151 | B2 * | 2/2009 | Yamamoto | G06F 16/40 |
| 8,477,903 | B2 * | 7/2013 | Wright | A61N 5/1071 |
| | | | | 378/156 |
| 8,986,186 | B2 * | 3/2015 | Zhang | A61N 5/103 |
| | | | | 600/1 |
| 9,486,646 | B2 * | 11/2016 | Paliwal | A61N 5/1042 |
| 9,835,737 | B1 * | 12/2017 | Czarnecki | G01T 1/208 |
| 9,987,504 | B2 * | 6/2018 | Nord | A61N 5/103 |
| 2009/0138415 | A1 * | 5/2009 | Lancaster | G06N 5/04 |
| | | | | 706/11 |
| 2011/0106418 | A1 * | 5/2011 | van der Merwe | G01C 21/12 |
| | | | | 701/532 |

(Continued)

OTHER PUBLICATIONS

Constantin, Magdalena et al.; "Modeling the TrueBeam Linac Using a CAD to Geant4 Geometry Implementation: Dose and IAEA-Compliant Phase Space Calculations," Med. Phys. 38 (7), Jul. 2011; p. 4018-4024.

*Primary Examiner* — Thai Q Phan
(74) *Attorney, Agent, or Firm* — Fitch, Even, Tabin & Flannery LLP

(57) ABSTRACT

A LINear particle ACcelerator (LINAC) simulator employs a Monte Carlo-based use of repeated random sampling to produce a simulated result representing use of a particular physical medical-services LINAC with particular corresponding real-world parameters. A browser-based user opportunity permits uploading at least some of those real-world parameters to employ when using the LINAC simulator to produce the simulated result. By one approach the browser-based user opportunity includes, at least in part, an opportunity to upload a file that contains information regarding geometrical positions for the particular physical LINAC. The opportunity to upload the file may, by one approach, presume using a file format that comprises a non-standard file format for the particular physical medical-services LINAC.

16 Claims, 2 Drawing Sheets

(56) References Cited

U.S. PATENT DOCUMENTS

| | | | |
|---|---|---|---|
| 2011/0249088 A1 | 10/2011 | Hannibal et al. | |
| 2012/0136194 A1* | 5/2012 | Zhang | A61N 5/103 600/1 |
| 2012/0250824 A1* | 10/2012 | Wright | A61N 5/1071 378/65 |
| 2014/0247919 A1* | 9/2014 | Zhang | A61B 6/025 378/62 |
| 2015/0235143 A1* | 8/2015 | Eder | G16H 50/50 706/12 |
| 2015/0324548 A1* | 11/2015 | Eder | G06Q 50/22 604/503 |
| 2016/0287906 A1* | 10/2016 | Nord | A61N 5/103 |

* cited by examiner

LINAC SIMULATOR

TECHNICAL FIELD

These teachings relate generally to LINear particle ACcelerators (LINAC's).

BACKGROUND

LINear particle ACcelerators (LINACs) are known in the art. Generally speaking, a LINAC is a type of particle accelerator that greatly increases the kinetic energy of charged subatomic particles or ions by subjecting the charged particles to a series of oscillating electric potentials along a linear beamline. A LINAC typically includes a particle source, a high voltage source for the initial injection of particles, a hollow pipe vacuum chamber having electrodes placed therein, and at least one source of radio frequency (RF) energy to energize those electrodes. Amongst other purposes, LINACs are used to provide medical services. For example, LINAC-based radiation therapy often serves as a basis for cancer therapy.

LINAC simulators are also known in the art. LINAC simulators permit researchers and others to run simulations to further research (regarding, for example, such things as modification of various delivery parameters, modification of the materials used, and so forth), to conduct quality assurance studies, and so forth. To support such uses a LINAC manufacturer may sometimes provide simplified summaries regarding specific LINAC systems that researchers can use to construct their own simulators. Even though the information provided is incomplete these arrangements are often burdened by non-disclosure requirements to protect the manufacturer's confidential information. Such an approach can be suboptimum at least for the reasons that the LINAC simulations are necessarily only approximate due to the lack of a sufficient amount of precise information and also because of the logistic difficulties that can arise due to a need to comply with potentially complex confidentiality requirements.

Web-based LINAC simulators are a recent development to attempt to remedy such concerns. By providing researchers and others with limited access to a remotely-located LINAC simulator, the manufacturer can more comfortably permit the LINAC simulator to comprise a more complete and accurate simulation of a corresponding real-world physical LINAC while simultaneously potentially lowering the logistical barriers to providing access to such a web-based LINAC simulator (at least in part because the physical arrangement can permit such a researcher to use the simulator without having access to exactly how the LINAC being simulated operates).

While the foregoing developments offer some useful advantages, there nevertheless remain a number of areas for improvement.

BRIEF DESCRIPTION OF THE DRAWINGS

The above needs are at least partially met through provision of the LINAC simulator described in the following detailed description, particularly when studied in conjunction with the drawings, wherein.

Figure 1:
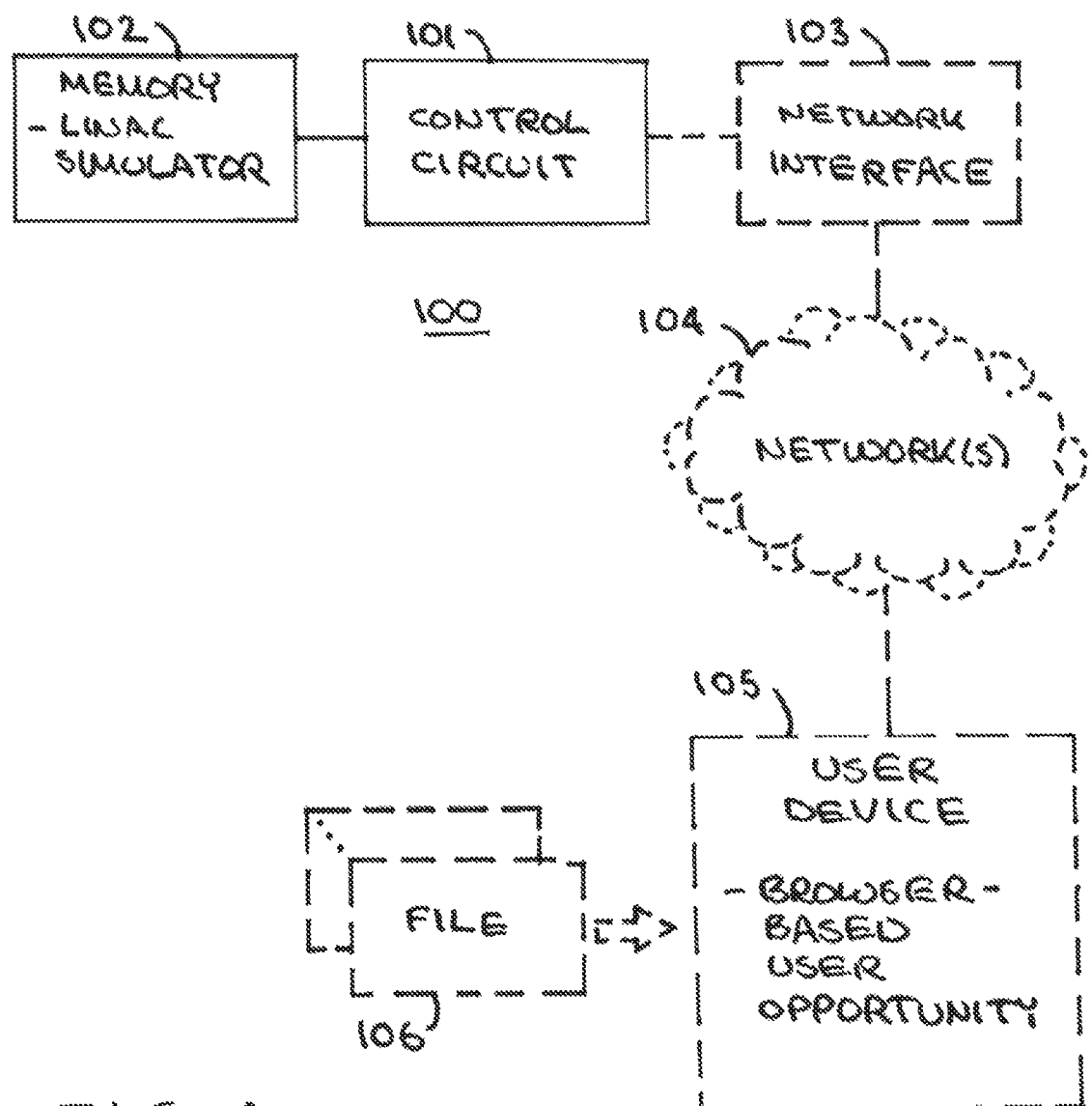
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, these various embodiments include providing a LINear particle ACcelerator (LINAC) simulator that employs a Monte Carlo-based use of repeated random sampling to produce a simulated result representing use of a particular physical medical-services LINAC with particular corresponding real-world parameters and then providing a browser-based user opportunity to upload at least some of those real-world parameters to employ when using the LINAC simulator to produce the simulated result. By one approach the browser-based user opportunity includes, at least in part, an opportunity to upload a file that contains information regarding geometrical positions for the particular physical LINAC. The opportunity to upload the file may, by one approach, presume using a file format that comprises a non-standard file format for the particular physical medical-services LINAC (such as a Developer Mode file format).

These teachings are highly flexible in practice. For example, by one approach the aforementioned geometrical positions for the particular physical LINAC can permissibly include at least one physical movement that is not approved by a relevant government agency (such as the Food and Drug Administration of the United States government) for use when providing medical services with the particular physical medical-services LINAC.

The aforementioned simulated results can be provided to a user via the aforementioned browser-based user opportunity if desired. Also if desired, the information regarding geometrical positions for the particular physical LINAC and the information representing a computed tomography (CT) scan for a given patient is used to produce the simulated result with the LINAC simulator. That simulated result can be compared with a previously-determined dosing result for a corresponding treatment plan to thereby facilitate assessing the quality of the treatment plan.

So configured, a LINAC simulator can be configured to simulate an actual real-world physical LINSC with high accuracy without the LINAC manufacturer being overly concerned that confidential information regarding how the simulated LINAC operates will be exposed to the detriment of the manufacturer.

These and other benefits may become clearer upon making a thorough review and study of the following detailed description. Referring now to the drawings, and in particular to FIG. 1, an illustrative enabling apparatus 100 that is compatible with many of these teachings will now be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to a LINAC simulator as discussed herein, this memory 102 can serve, for example, to non-transitorily store the various computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

In this example the control circuit 101 can also operably couples to an optional network interface 103 that in turn can communicatively couple to one or more external networks 104 (including but not limited to the Internet, a global network of networks of interconnected mainframe, personal, and wireless computer networks that use the Internet protocol suite (TCP/IP) to link billions of devices worldwide). So configured the control circuit 101 can communicate with other elements (both within the apparatus 100 and external thereto) via the network interface 103. Network interfaces, including both wireless and non-wireless platforms, are well understood in the art and require no particular elaboration here.

As noted above, the aforementioned memory 102 has a LINAC simulator stored therein. In this particular example the LINAC simulator employs a Monte Carlo-based use of repeated random sampling to produce a simulated result that represents use of a particular physical medical-services LINAC (i.e., a real-world LINAC as versus, for example, a theoretical LINAC) with particular corresponding real-world parameters. Monte Carlo methods that rely on repeated random sampling are well known and require no further elaboration here. These teachings will accommodate other approaches in these regards if desired. For example, the simulator may employ analytic methods that rely on superposition-convolution algorithms and/or analytic anisotropic algorithms.

Figure 2:
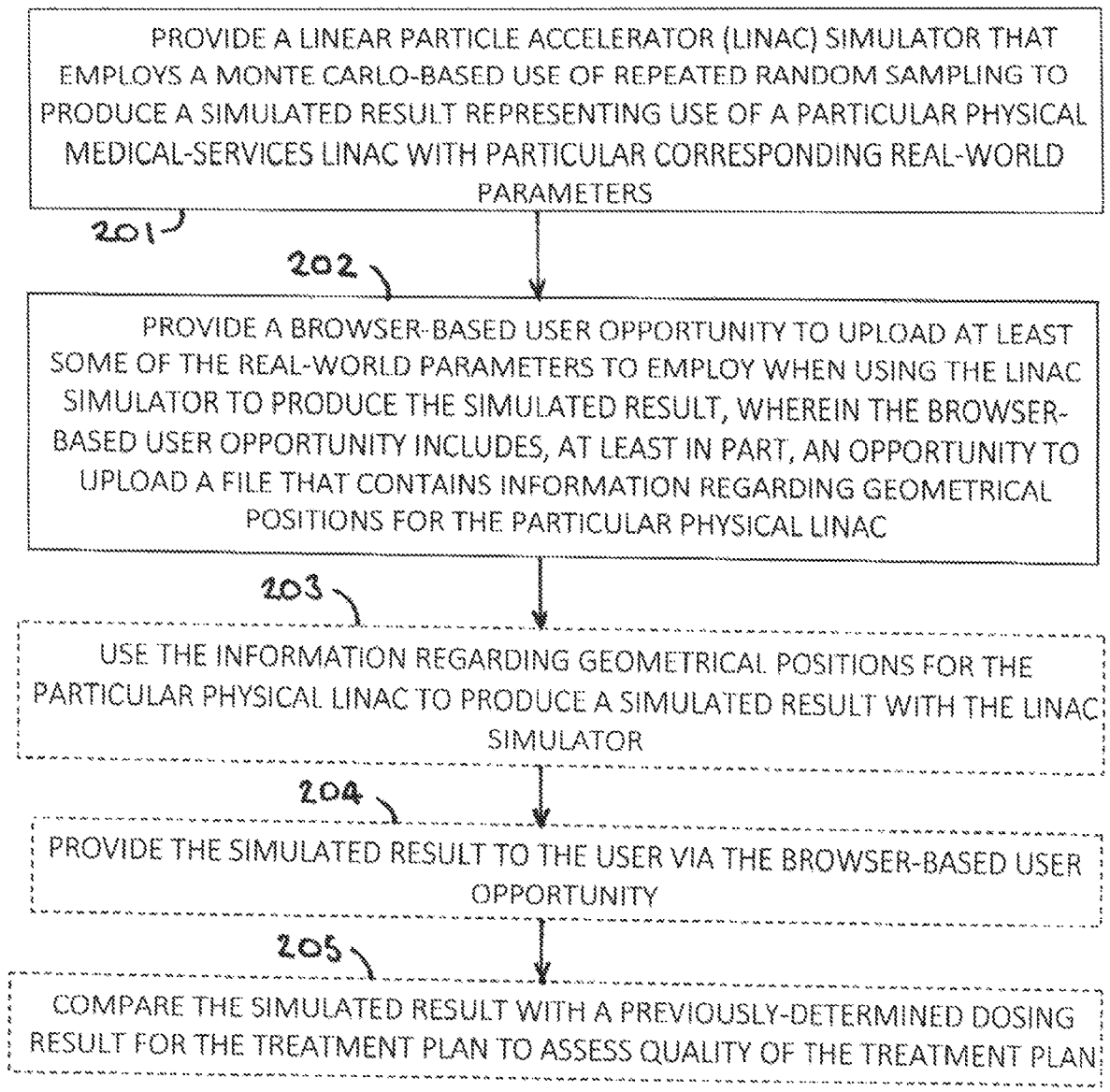
FIG. 2 comprises a flow diagram as configured in accordance with various embodiments of these teachings.

Referring now to both FIGS. 1 and 2, per the process 200 of FIG. 2 the aforementioned LINAC simulator includes corresponding supporting components that effect the requirements of block 201 by providing a LINAC simulator that employs a Monte Carlo-based use of repeated random sampling to produce a simulated result representing use of a particular physical medical co-services LINAC with particular corresponding real-world parameters. As already noted above, this LINAC simulator does not serve in these regards to represent a generic LINAC or an imaginary LINAC. Instead, the LINAC simulator is configured to simulate a particular real-world physically-embodied medical-services LINAC.

At block 202 this process 200 provides a browser-based user opportunity (via, for example, the aforementioned user device 105 where the control circuit 101 is configured as a server such as an Internet server). This browser-based user opportunity can include any of a variety of approaches for conveying information from the control circuit 100 and or other remote sources to the user device 105.

This browser-based user opportunity can also include any of a variety of mechanisms by which the user can enter data or instructions (pertaining, for example, to use of the LINAC simulator). In particular, this browser-based user opportunity can be configured to accommodate the user uploading at least some real-world parameters to employ when using the LINAC simulator to produce the aforementioned simulated result.

Without intending any particular limitations in regards, this browser-based user opportunity can specifically include, at least in part, an opportunity to specify parameters regarding the treatment beam (for example, that the treatment beam is a 6 MV photon beam) and corresponding information such as the nature of the flattening filter (if employed), the nature of the target, and the energy of the incident electron beam. Other provided information can include information regarding the phantom (i.e., the material that will be absorbing the dose). This information can be general in nature (for example, by specifying a box of a particular size that is filled with water) or the material and density of that material can be specified for each voxel to note but two examples in these regards.

This browser-based user opportunity can also specifically include, at least in part, an opportunity to upload a file 106 that contains information regarding geometrical positions for the particular physical LINAC (for example, the coordinates of axes of motion as correspond to gantry positions and so forth). By one approach, the file format to be used when uploading the file 106 can comprise a non-standard file format for physical medical-services LINACs. One salient example in these regards is the Developer Mode file format (a format that is an extension of extensible markup language (XML)) available from Varian Medical Systems in conjunction with its TrueBeam system.

By one approach the geometrical positions for the particular physical LINAC can specify or otherwise relate to one or more movements of the particular physical medical-services LINAC. For example, such a movement can correspond to at least one axis of motion for the particular physical medical-services LINAC.

If desired, the uploaded geometrical positions can permissibly include at least one movement that is not approved by a relevant government agency (such as the Food and Drug Administration of the United States government) for use when providing medical services with the particular physical medical-services LINAC. As used herein, this reference to "permissibly" shall be understood to mean that the LINAC simulator can receive, accept, and utilize non-approved movements when producing simulated results. Such an accommodation can be very useful to researchers and others who seek to better understand capabilities and/or limitations of a particular physical LINAC notwithstanding that one or more movements of interest may not be presently approved or may even be presently disapproved.

These teachings are flexible and will accommodate various approaches depending upon the needs and/or requirements of a given application setting. By one approach, for example, the aforementioned information regarding geometrical positions for a particular physical LINAC can be derived from a treatment plan for a given patient and wherein the information further includes information representing a computed tomography (CT) scan for that given patient.

At optional block 203 this process 200 provides for using information regarding geometrical positions for the particular physical LINAC to produce a simulated result with the LINAC simulator. When the information regarding geometrical missions is derived from a treatment plan and a CT scan for a given patient as noted above, this activity can comprise using information regarding geometrical positions for the particular physical LINAC and the information representing the produce the simulated result if desired. Generally speaking, the output of the simulation can comprise a dose distribution with respect to a phantom target (the phantom being the virtual object that receives the virtual dose). Other output possibilities include intermediate results in the form of lists of particles (so-called phase space files) that are upstream of the phantom.

At optional block 204 the control circuit 101 provides the user (at the above mentioned device 100) the simulated result via the aforementioned browser-based user opportunity. The simulated result can be provided in a variety of forms as desired, and can include abbreviated or detailed textual and/or graphic/image-based presentations thereof.

At optional block 205 the control circuit 101 compares the simulated result with other standards, thresholds, or the like. By one approach, for example, the control circuit 101 compares the simulated result with a previously-determined dosing result for the above-mentioned treatment plan to thereby assess the quality of that treatment plan. This might comprise, for example, comparing a calculation of dose distributions using the aforementioned simulation approach and also using commercially-available software such as the Eclipse treatment planning system offered by Varian Medical Systems, Inc. When the results for both independent approaches agree the user will have increased confidence in the calculations.

So configured, confidential information regarding the operating specifics of real-world physical LINACs is not only readily concealed and thereby protected, but the ability of a given simulation to operate using real-world information provided by a given user is greatly enhanced. By simply uploading a file (or files, as the case may be) that specifies such things as the LINAC geometrical positions of interest, the simulation can provide simulation results of both great real-world accuracy and great relevance to the user's purposes.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A method comprising:
providing a LINear particle ACcelerator (LINAC) simulator that employs a Monte Carlo-based use of repeated random sampling to produce a simulated result representing use of a particular physical medical-services LINAC with particular corresponding real-world parameters;
providing a browser-based user opportunity to upload at least some of the real-world parameters to employ when using the LINAC simulator to produce the simulated result, wherein the browser-based user opportunity includes, at least in part, an opportunity to upload a file that contains information regarding geometrical positions for the particular physical LINAC and wherein the opportunity to upload the file comprises an opportunity to use a file format that comprises a Developer Mode file format that is a non-standard file format for the particular physical medical-services LINAC.

2. The method of claim 1 wherein the geometrical positions can permissibly include at least one movement that is not approved by a relevant governmental agency for use when providing medical services with the particular physical medical-services LINAC.

3. The method of claim 2 wherein the relevant governmental agency is the Food and Drug Administration of the United States government.

4. The method of claim 2 wherein the at least one movement corresponds to at least one axis of motion for the particular physical medical-services LINAC.

5. The method of claim 1 further comprising:
using the information regarding geometrical positions for the particular physical LINAC to produce a simulated result with the LINAC simulator.

6. The method of claim 5 further comprising:
providing the simulated result to the user via the browser-based user opportunity.

7. The method of claim 1 wherein the information regarding geometrical positions for the particular physical LINAC is derived from a treatment plan for a given patient and wherein the information further includes information representing a computed tomography (CT) scan for the given patient.

8. The method of claim 7 further comprising:
using the information regarding geometrical positions for the particular physical LINAC and the information representing the CT scan to produce a simulated result with the LINAC simulator;
comparing the simulated result with a previously-determined dosing result for the treatment plan to assess quality of the treatment plan.

9. An apparatus comprising:
a memory having stored therein a LINear particle ACcelerator (LINAC) simulator that employs a Monte Carlo-based use of repeated random sampling to produce a simulated result representing use of a particular physical medical-services LINAC with particular corresponding real-world parameters;

a control circuit operably coupled to the memory and configured to provide a browser-based user opportunity to upload at least some of the real-world parameters to employ when using the LINAC simulator to produce the simulated result, wherein the browser-based user opportunity includes, at least in part, an opportunity to upload a file that contains information regarding geometrical positions for the particular physical LINAC and wherein the opportunity to upload the file comprises an opportunity to use a file format that comprises a Developer Mode file format that is a non-standard file format for the particular physical medical-services LINAC.

10. The apparatus of claim 9 wherein the geometrical positions can permissibly include at least one movement that is not approved by a relevant governmental agency for use when providing medical services with the particular physical medical-services LINAC.

11. The apparatus of claim 10 wherein the relevant governmental agency is the Food and Drug Administration of the United States government.

12. The apparatus of claim 10 wherein the at least one movement corresponds to at least one axis of motion for the particular physical medical-services LINAC.

13. The apparatus of claim 9 wherein the control circuit is further configured to use the information regarding geometrical positions for the particular physical LINAC to produce a simulated result with the LINAC simulator.

14. The apparatus of claim 13 wherein the control circuit is further configured to provide the simulated result to the user via the browser-based user opportunity.

15. The apparatus of claim 9 wherein the information regarding geometrical positions for the particular physical LINAC is derived from a treatment plan for a given patient and wherein the information further includes information representing a computed tomography (CT) scan for the given patient.

16. The apparatus of claim 15 wherein the control circuit is further configured to:
 use the information regarding geometrical positions for the particular physical LINAC and the information representing the CT scan to produce a simulated result with the LINAC simulator;
 compare the simulated result with a previously-determined dosing result for the treatment plan to assess quality of the treatment plan.

* * * * *